US011883084B2

(12) United States Patent
Pacheco et al.

(10) Patent No.: US 11,883,084 B2
(45) Date of Patent: Jan. 30, 2024

(54) WATER-SOLUBLE STICKER FOR MARKING GLASSWARE

(71) Applicant: Glass Tats LLC, Larkspur, CA (US)

(72) Inventors: Maya Pacheco, Larkspur, CA (US); Corinne Golden, Corte Madera, CA (US)

(73) Assignee: Glass Tats LLC, Larkspur, CA (US)

( * ) Notice: Subject to any disclaimer, the term of this patent is extended or adjusted under 35 U.S.C. 154(b) by 64 days.

(21) Appl. No.: 17/239,852

(22) Filed: Apr. 26, 2021

(65) Prior Publication Data

US 2021/0343190 A1 Nov. 4, 2021

Related U.S. Application Data

(60) Provisional application No. 63/018,568, filed on May 1, 2020.

(51) Int. Cl.
*G09F 3/00* (2006.01)
*G09F 3/02* (2006.01)
*A61B 17/92* (2006.01)
*A61B 17/00* (2006.01)

(52) U.S. Cl.
CPC .......... *A61B 17/921* (2013.01); *G09F 3/0291* (2013.01); *A61B 2017/00477* (2013.01); *G09F 2003/0226* (2013.01); *G09F 2003/0242* (2013.01)

(58) Field of Classification Search
CPC ........ A61B 17/921; A61B 2017/00477; G09F 3/0291; G09F 3/02; G09F 3/18; G09F 2003/0226; G09F 2003/0242; G09F 5/04
See application file for complete search history.

(56) References Cited

U.S. PATENT DOCUMENTS

| 4,444,839 A | 4/1984 | Dudzik et al. |
| 8,747,929 B2 | 6/2014 | Milliorn |
| 9,418,576 B2 | 8/2016 | Franklin |

FOREIGN PATENT DOCUMENTS

| EP | 2120228 A2 * | 11/2009 | ............. B32B 37/12 |
| JP | 3190654 U * | 5/2014 | |

OTHER PUBLICATIONS

Hallmark LEGO Birthday Card with Stickers via Amazon; available Jan. 25, 2019 (Year: 2019).*

* cited by examiner

*Primary Examiner* — Laura C Powers
(74) *Attorney, Agent, or Firm* — Smith Baluch LLP

(57) ABSTRACT

At parties and other social gatherings, drinks are typically served in non-descript glassware. As a result, patrons may be unable to distinguish their glass from others once they are set down on a table. Unintentionally swapping glasses can be unsanitary and wasteful (increasing costs for the host of the event). To solve these problems, the inventors have created an easy way for people to mark their glassware with individualized stickers that are easy to remove at the conclusion of a gathering.

The invention is water-soluble stickers that are designed around the theme of the gathering. Guests select from a set of unique stickers and adhere one to their glass—they work on all glassware (even without stems). At the end of the gathering, the host can easily remove the drink markers by running the glassware under water or by placing them in the dishwasher as they normally would.

21 Claims, 5 Drawing Sheets

Exploded View

WATER-SOLUBLE STICKER FOR MARKING GLASSWARE

CROSS-REFERENCE TO RELATED APPLICATIONS

All priority benefits under 35 USC 119(e) of Provisional Patent Application Ser. No. 63/018,568, filed May 1, 2020 are hereby claimed and the contents thereof in their entirety incorporated herein by reference.

BACKGROUND

At parties and other social gatherings, drinks are typically served in non-descript glassware. As a result, patrons may be unable to distinguish their glass from others once they are set down on a table. Unintentionally swapping glasses can be unsanitary and may contribute to the spread of viruses and/or other pathogens. In other cases, if a person cannot identify their own glass, they may abandon it and simply get another, which can be wasteful and increase costs for the host of the event.

Attempts have been made in the past for adding identifying characteristics to glassware, such as stickers and charms. However, charms can be difficult to remove before being inserted in a dishwasher (and failure to remove them may cause them to fall off in the dishwasher, which can lead to damage of dishwasher components). Previous attempts to use stickers required a burdensome chore of removing the sticker and its adhesive residue by hand, sometimes with the aid of solvents. In addition, the design of the stickers was generic and not easily customizable to reflect the theme of the gathering.

SUMMARY OF THE INVENTION

To solve the above-described problems the inventors have created an easy way for people to mark their glassware with individualized stickers that are easy to remove at the conclusion of a social gathering. The invention is directed to a water-dissolvable sticker package which contains at least one water-dissolvable sticker sheet, on which are printed at least one water-dissolvable sticker that can be removed from the water-dissolvable sticker sheet and placed onto a glass. To remove the sticker, the glass can be placed in a dishwasher or exposed to water for a brief period of time.

Additionally, the inventors have created two unique embodiments for displaying the water-dissolvable sticker package. In the first embodiment, the sticker sheet is attached to a rectangular cardstock backing, which is scored to allow the backing to be bent at an angle which allows the water-dissolvable sticker sheet to be displayed in an upright or semi-upright position. In the second embodiment, the sticker sheet is attached to a gift tag shaped cardstock backing with an attachment means (such as a string, ribbon, or wire) that is run through the backing and allows the water-dissolvable sticker package to be attached to an object, such as a wine bottle.

DETAILED DESCRIPTION

Figure 1:
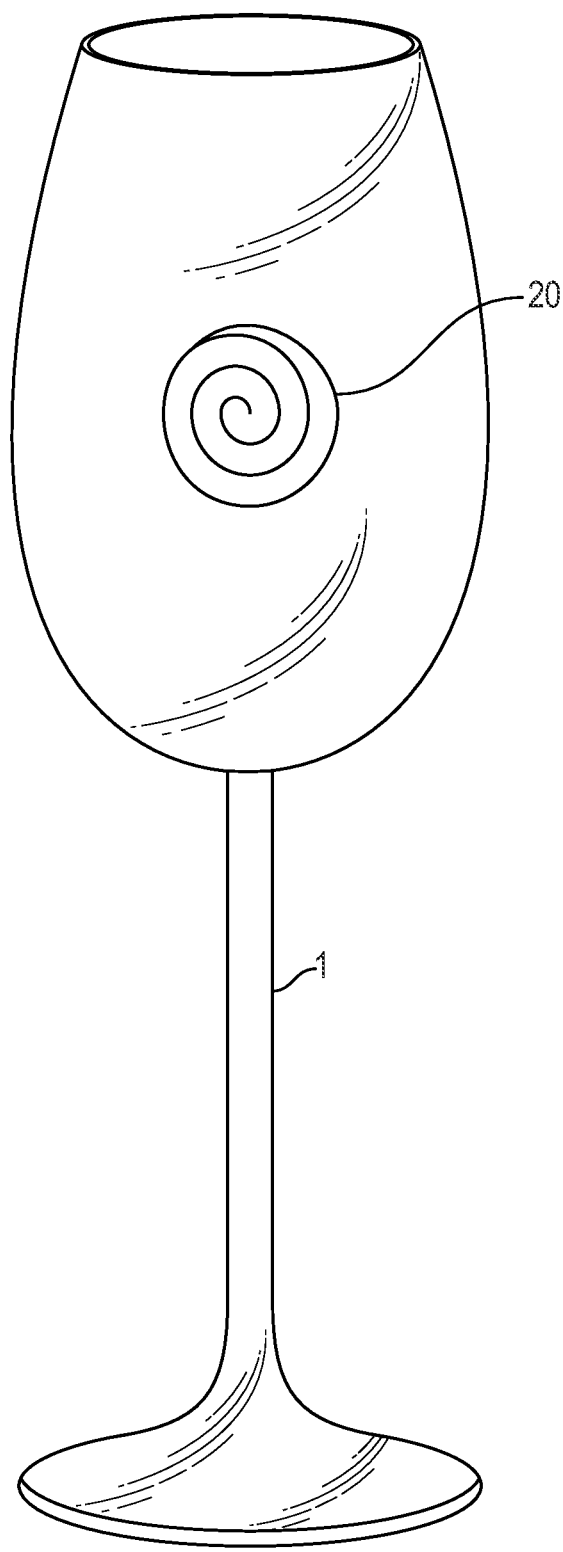
FIG. 1 shows a glassware to which a water-dissolvable sticker is attached.

FIG. 1 shows glassware (1) with a water-dissolvable sticker (20) attached. Although glassware is depicted, Inventors envision the water-dissolvable sticker (20) could likewise be applied to dinnerware (not shown). The water-dissolvable sticker (20) is applied as one would apply any type of ordinary sticker, and will be described in greater detail below. The water-dissolvable sticker (20) allows a user to recognize his or her glass in a social gathering where drinks are served, such as a party.

Figure 2A:
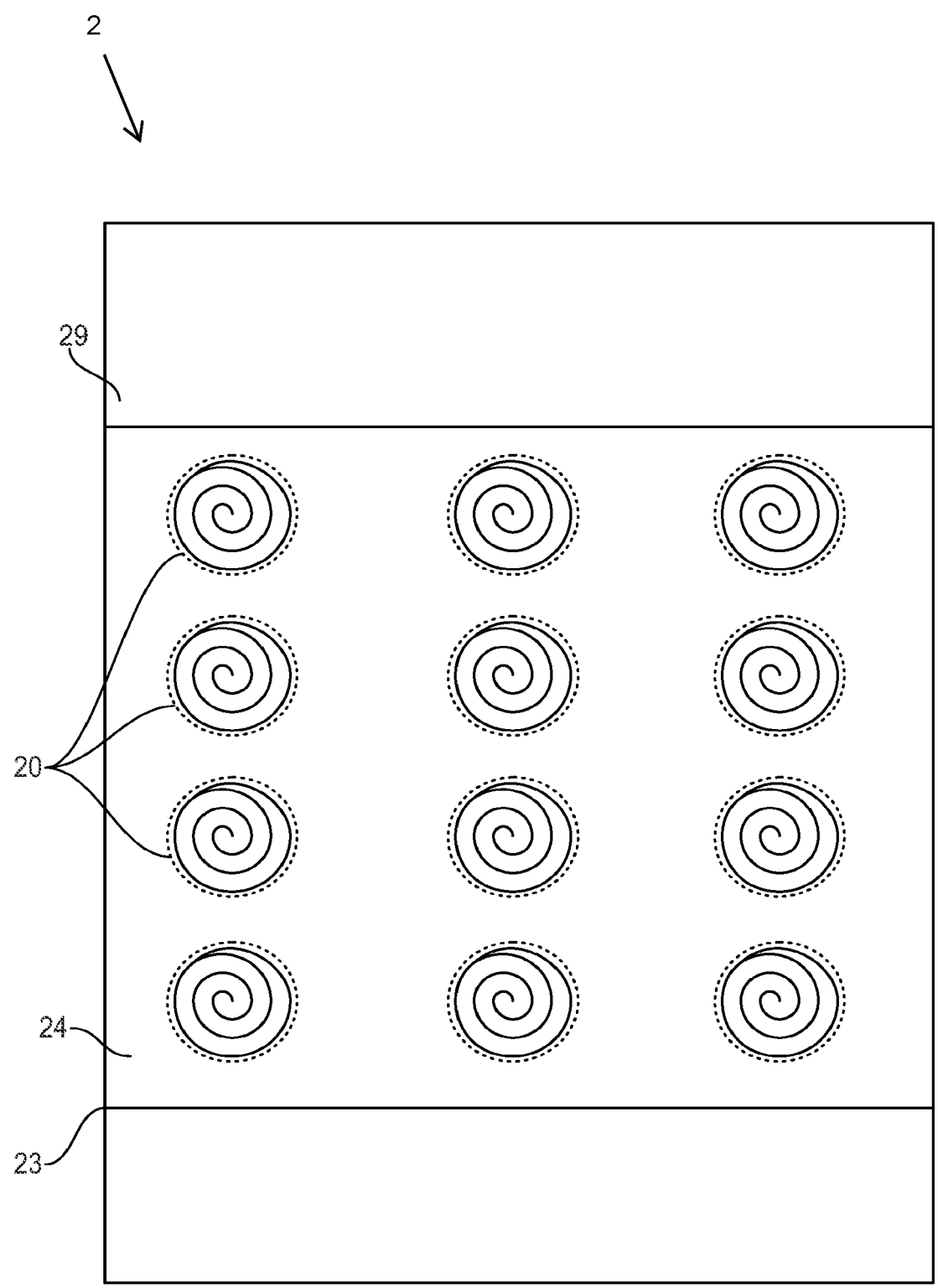
FIG. 2A shows the water-dissolvable sticker package of the first embodiment.
Figure 2B:
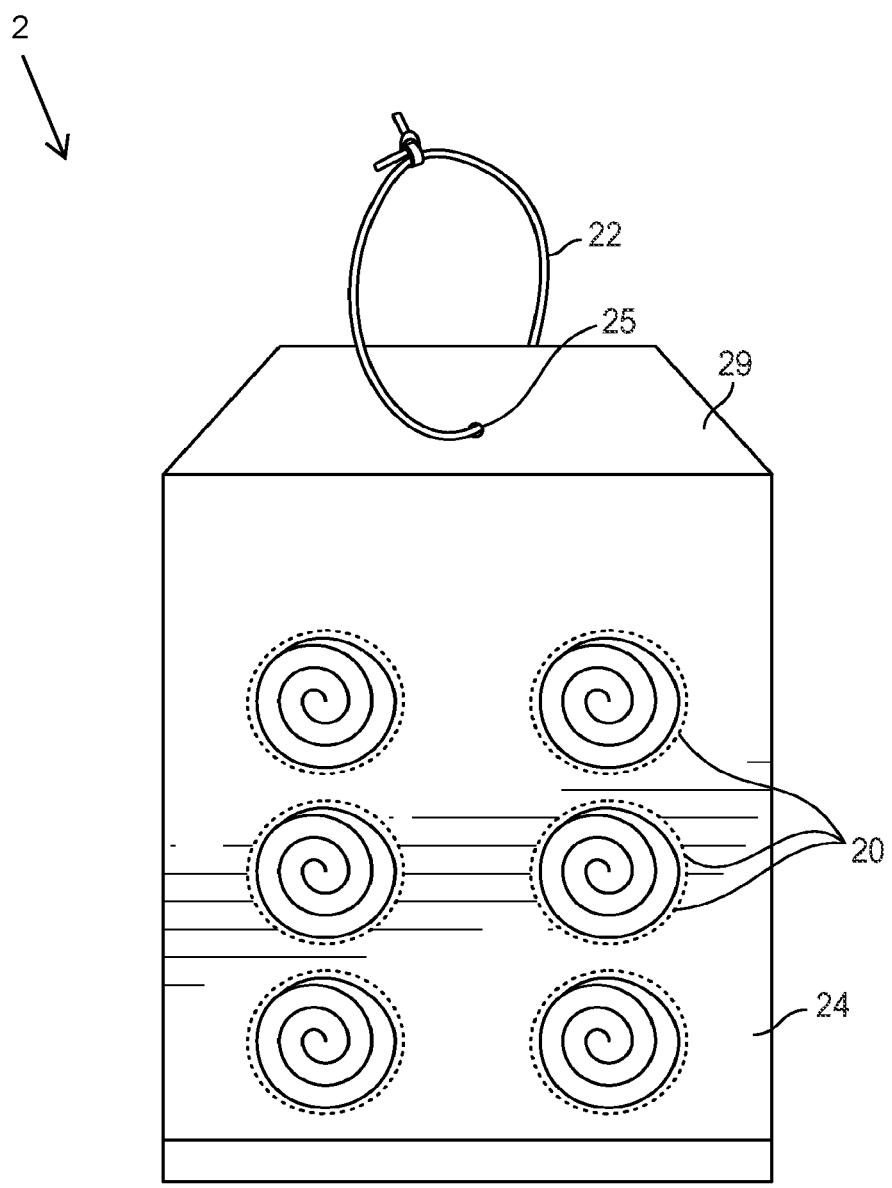
FIG. 2B shows the water-dissolvable sticker package of the second embodiment
Figure 3:
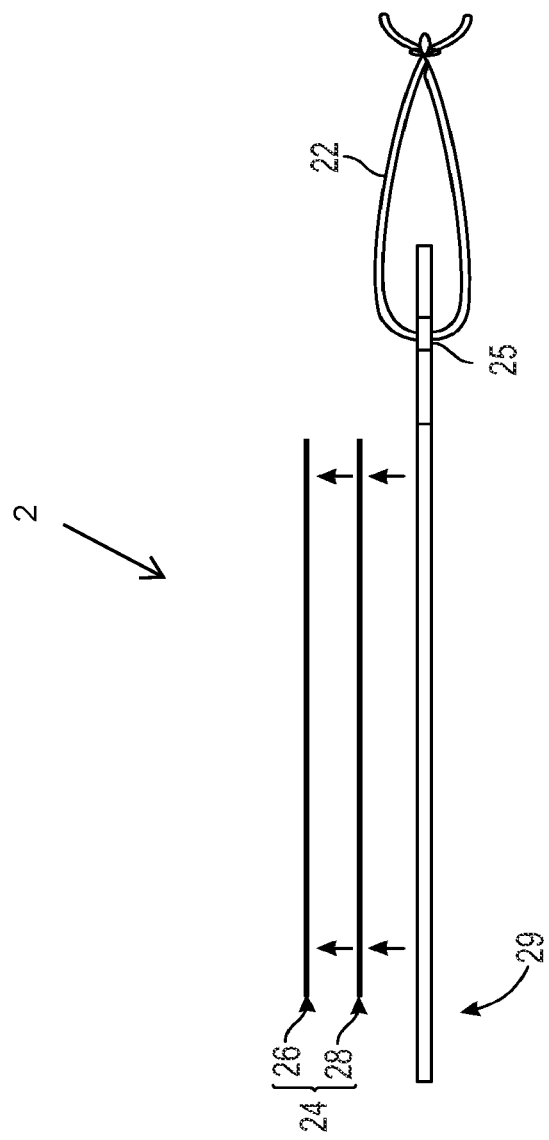
FIG. 3 shows an exploded view of the water-dissolvable sticker package in the second embodiment.

FIGS. 2A, 2B & 3 show a water-dissolvable sticker package (2). The water-dissolvable sticker package (2) contains one or more water-dissolvable sticker sheets (24). As can best be seen in FIG. 3, each water-dissolvable sticker sheet (24) is composed of a water-dissolvable paper (26) and a non-stick backer (28). A water-dissolvable adhesive (not shown) is applied to one side of the water dissolvable paper (26). The water-dissolvable paper (26) is then applied to the non-stick backer (28) so that the water-dissolvable adhesive is prevented from sticking to unintended surfaces and later allows individual water-dissolvable stickers (20) to be removed from the water-dissolvable sticker sheet (24). Water dissolvable paper (26) can be purchased from suppliers, such as SmartSolve Industries of Bowling Green, Ohio. Inventors have experimented with different thicknesses and determined that a 4-mil thickness is ideal.

Once the sticker sheet (24) has been created, ink can be applied to the water-dissolvable paper (26) to create graphics for water-dissolvable stickers (20). Inventors have found that an inkjet printer works well for this task, because it allows for the use of color when designing and creating unique water-dissolvable stickers (20). Alternatively, instead of ink, a thermal printer could be used in conjunction with a water-dissolvable thermal label paper (one type of which is currently sold by SmartSolve of Bowling Green, Ohio) to print graphics on the water-dissolvable paper (26).

After printing, the water-dissolvable paper (26) is cut to allow individual water-dissolvable stickers (20) to be removed from the water-dissolvable sticker sheet (24). Although different methods for cutting out individual stickers can be used (which are known to the art and will not be described in greater detail, but are nonetheless envisioned as being within the scope of the invention), Inventors prefer to use the "kiss-cut" technique, under which only the water-dissolvable paper (26) is cut, not the underlying non-stick backer (28). Kiss-cutting the water-dissolvable stickers (20) has the added benefit of allowing a plurality of water-dissolvable stickers (20) to remain on a single water-dissolvable sticker sheet (24) until removal and use.

Figure 4:
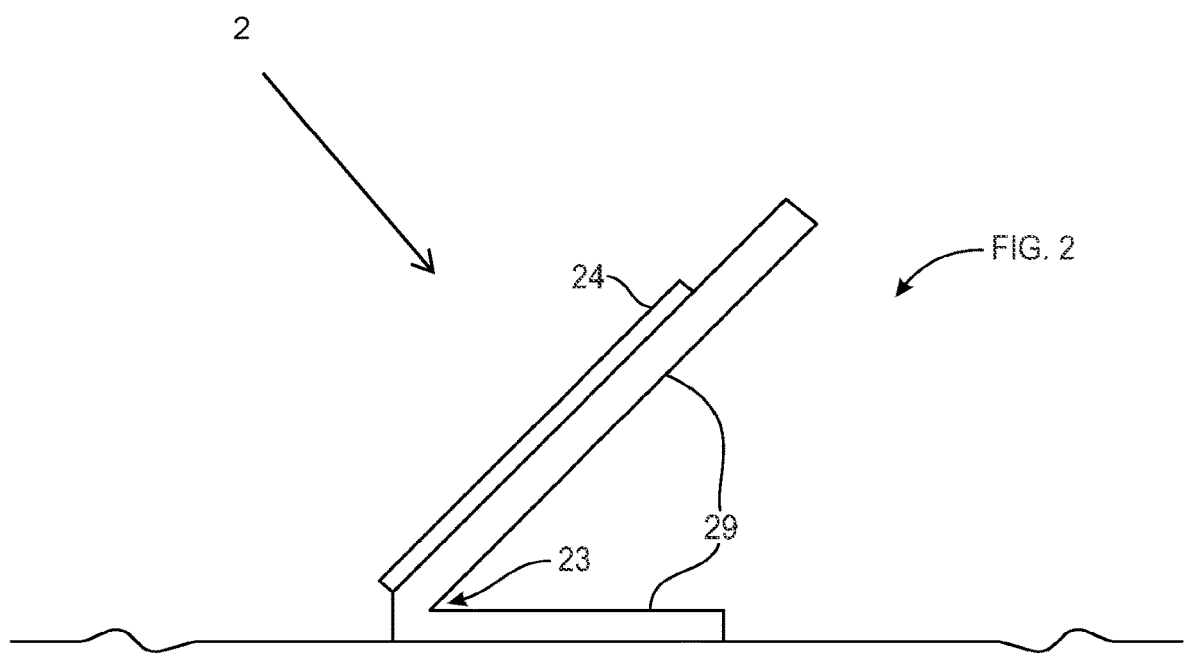
FIG. 4 shows the water-dissolvable sticker package in a semi-upright position.

Behind the at least one water-dissolvable sticker sheet (24) is a backing (29), which adds rigidity to the water-dissolvable sticker packages (2) and helps protect the at least one water dissolvable sticker sheet (24) from damage during transport and/or storage. The backing can be made from any type of flat stock, which could include paperboard, cardboard, paper-stock, or plastic. In the first embodiment, the backing (29) can be scored along score line (23) to allow backing (29) to be folded, which allows the water-dissolvable sticker package (2) to be displayed in an upright or semi-upright position, as shown in FIG. 4. The term "scoring" is intended to be broadly interpreted to include any type of mechanical process which increases the foldability of flat stock, and includes at least: etching, perforating, slicing, or indenting. The backing can be adhered to the back of the water-dissolvable sticker sheet (24) using glue, tape, or a mechanical fastener, such as a staple or rivet.

To allow for the folding of the backing (29), it typically has a larger lengthwise dimension than the water-dissolvable sticker sheet (24). Alternatively, in the second embodiment, the backing (29) is cut such that it is shaped to resemble a gift tag, as shown in FIG. 2B. In the second embodiment, the water-dissolvable sticker package (2) to be attached to an object, such as a wine bottle, an aperture (25) is cut into the backing (29), through which an attachment means (22) is passed, which is then secured to the object. The attachment means can be a ribbon, string, wire, zip-tie, or something similar.

To enclose the water-dissolvable sticker package (2), a transparent wrapper (not shown) is placed around the water-dissolvable sticker package (2). Inventors prefer the use of cellophane, but other types of transparent or semi-transparent packaging are known in the art and are within the scope of the invention.

Having disclosed the product and the method in which it is manufactured, Inventors will now describe the product's method of use. A user, such as the host of a social gathering, can display the water-dissolvable sticker package (2) in at least one of two ways. First, a user can attach the water-dissolvable sticker package (2) to an object, such as a wine bottle, using an attachment means (22) (such as a ribbon, string, wire, zip-tie, or similar structure), which is looped through the aperture (25) in at least the backing (29). The aperture (25) may also pass through other elements of the water-dissolvable sticker package (2), such as at least one water-dissolvable sticker sheet (24) and/or the transparent wrapper (not shown).

Second, as shown in FIG. 4, a user can display the water-dissolvable sticker package (2) by bending the backing (29) along the score line (23), such that a portion of the backing (29) is at an angle to the remaining portion of the backing (29). By bending a portion of the backing (29), the water-dissolvable sticker package (2) can be placed in an upright or semi-upright position, which allows the water-dissolvable sticker sheet (24) to be displayed.

An individual sticker (20) can be peeled off of the water-dissolvable sticker sheet (24) and adhered to glassware (1), such as a wine glass, beer mug, shot glass, tumbler, etc. Since each individual sticker (20) typically has a unique design, the sticker (20) allows a person to easily identify their own glass. In other situations, such as weddings, a generic sticker (20) can be placed on the glassware with a graphic directed to the event, such as "Congratulations [Bride's Name] and [Groom's Name]!" This allows glassware to be personalized for a particular one-time event at a reduced cost because a water dissolvable sticker is cheaper than producing a personalized glass.

At the end of the social gathering, the sticker (20) can be easily removed by placing the glassware in a dishwasher or by simply exposing the sticker to water for a period of time. The time necessary for the sticker (20) to dissolve varies based on the degree of agitation and temperature of the water, but typically takes 5-10 seconds.

LIST OF SYMBOLS

1: Glassware
2: Sticker Package
20: Individual Sticker
22: Attachment Means
23: Score Line
24: Water-dissolvable Sticker Sheet
25: Aperture
26: Water-dissolvable Label Paper
28: Non-stick Backer
29: Backing

We claim:

1. A sticker package comprising:
   a water-dissolvable sticker sheet having at least one sticker for application to glassware, the water-dissolvable sticker sheet comprising:
   a water-dissolvable paper,
   a water-dissolvable adhesive applied to one side of the water-dissolvable paper, and
   an inkjet-printed design applied to an opposing side of the water-dissolvable paper to create a design for the at least one sticker,
   a non-stick backer to which the water-dissolvable paper can be temporarily adhered;
   and a backing, wherein the backing is scored to allow the backing to be bent to hold the sticker package in an upright or semi-upright position.

2. The sticker package of claim 1, further comprising a transparent wrapper which encloses the sticker package.

3. The sticker package of claim 1, wherein the water-dissolvable paper is kiss cut after being applied to the non-stick backer to create the at least one sticker, such that a single sticker can be peeled away from the water-dissolvable sticker sheet.

4. The sticker package of claim 1, wherein the thickness of the water-dissolvable paper is approximately 4 mils.

5. The sticker package of claim 1, wherein the water-dissolvable sticker sheet is adhered to the backing.

6. A method of making a sticker package including at least one sticker for application to glassware, the method comprising:
   creating a sticker sheet by:
      applying water-dissolvable adhesive to a first side of a water-dissolvable paper,
      temporarily adhering the first side of the water-dissolvable paper to a non-stick backer,
      inkjet printing designs to a second side of the water-dissolvable paper to create designs for the at least one sticker, and
      kiss cutting the water-dissolvable paper to create the at least one sticker placing a backing under the sticker sheet to form the sticker package; and
   scoring the backing to allow the backing to be bent to hold the sticker sheet in an upright or semi-upright position.

7. The method of claim 6, further comprising:
   placing the sticker sheet and the backing in a transparent wrapper, which encloses the sticker sheet and the backing.

8. The method of claim 6, further comprising:
   adhering the sticker sheet to the backing.

9. A method of using the sticker package of claim 1, comprising:
   removing the at least one sticker from the water-dissolvable sticker sheet and applying the at least one sticker to glassware.

10. The method of claim 9, further comprising:
    removing the at least one sticker from the glassware by placing the glassware in a dishwasher.

11. The method of claim 9, further comprising:
removing the at least one sticker from the glassware by applying water to the sticker until the at least one sticker dissolves.

12. The method of claim 6, wherein the at least one sticker comprises a plurality of stickers and each of the plurality of stickers has a unique design.

13. The method of claim 6, wherein the at least one sticker comprises a plurality of stickers and each of the plurality of stickers is configured to be personalized for identification of a person's glass.

14. The method of claim 6, wherein inkjet printing the designs comprises applying colored ink with an inkjet printer.

15. The method of claim 6, wherein the backing is longer than the sticker sheet.

16. The method of claim 15, wherein placing the backing under the sticker sheet comprises placing the sticker sheet on the backing between a first edge of the backing and a second edge of the backing and scoring the backing comprises forming a score line between the first edge of the backing and an edge of the sticker sheet.

17. The sticker package of claim 1, wherein the at least one sticker comprises a plurality of stickers and each of the plurality of stickers has a unique design.

18. The sticker package of claim 1, wherein the at least one sticker comprises a plurality of stickers and each of the plurality of stickers is configured to be personalized for identification of a person's glass.

19. The sticker package of claim 1, wherein the inkjet-printed design is printed in colored ink.

20. The sticker package of claim 1, wherein the backing is longer than the water-dissolvable sticker sheet.

21. The sticker package of claim 20, wherein the water-dissolvable sticker sheet is between a first edge of the backing and a second edge of the backing and the backing is scored along a score line between the first edge of the backing and an edge of the water-dissolvable sticker sheet.

\* \* \* \* \*